US00PP18611P2

(12) United States Plant Patent
Reinhoud

(10) Patent No.: US PP18,611 P2
(45) Date of Patent: Mar. 18, 2008

(54) **NEW GUINEA *IMPATIENS* PLANT NAMED 'ODYHERMES'**

(50) Latin Name: *Impatiens hawkeri*
Varietal Denomination: Odyhermes

(75) Inventor: Poula Reinhoud, Leiden (NL)

(73) Assignees: Agriom B.V., De Kwakel (NL); Florema Young Plants B.V., Aalsmeer (NL)

( * ) Notice: Subject to any disclaimer, the term of this patent is extended or adjusted under 35 U.S.C. 154(b) by 0 days.

(21) Appl. No.: 11/444,245

(22) Filed: May 31, 2006

(51) Int. Cl.
*A01H 5/00* (2006.01)

(52) U.S. Cl. ..... Plt./318
(58) Field of Classification Search ..... Plt./318
See application file for complete search history.

(56) References Cited

PUBLICATIONS

Agriom B.V. Contact [online], [retrieved on May 16, 2007]. Retrieved from the Internet <http://www.agriom.nl/contact–engl.htm> 2 pages.*
Upov–rom Plant Variety Database 2006/04, GTI Jouve Retrieval Software, Citation for New Guinea *Impatiens* 'Odyhermes', one page.*

* cited by examiner

*Primary Examiner*—Kent Bell
*Assistant Examiner*—June Hwu
(74) *Attorney, Agent, or Firm*—C. A. Whealy

(57) ABSTRACT

A new and distinct cultivar of New Guinea *Impatiens* plant named 'Odyhermes', characterized by its upright, outwardly spreading and mounded plant habit; vigorous and freely branching habit; dense and bushy growth habit; dark green-colored leaves; freely flowering habit; and large dark red-colored flowers that are positioned above and beyond the foliage.

1 Drawing Sheet

Botanical designation: *Impatiens hawkeri.*
Cultivar denomination: 'Odyhermes'.

BACKGROUND OF THE INVENTION

The present invention relates to a new and distinct cultivar of New Guinea *Impatiens* plant, botanically known as *Impatiens hawkeri,* and hereinafter referred to by the name 'Odyhermes'.

The new *Impatiens* is a product of a planned breeding program conducted by the Inventor in De Kwakel, The Netherlands. The objective of the breeding program was to develop new drought-tolerant New Guinea *Impatiens* cultivars with numerous large flowers and attractive foliage and flower coloration.

The new *Impatiens* originated from a cross-pollination made by the Inventor in May, 2002, of a proprietary selection of *Impatiens hawkeri* identified as code number 200024, not patented, as the female, or seed, parent with a proprietary selection of *Impatiens hawkeri* identified as code number 200142-01, not patented, as the male, or pollen, parent. The cultivar Odyhermes was discovered and selected by the Inventor as a flowering plant within the progeny of the stated cross-pollination in a controlled environment in De Kwakel, The Netherlands in July, 2003.

Asexual reproduction of the new cultivar by terminal cuttings propagated in a controlled environment in De Kwakel, The Netherlands since October, 2003 has shown that the unique features of this new *Impatiens* are stable and reproduced true to type in successive generations of asexual reproduction.

SUMMARY OF THE INVENTION

The cultivar Odyhermes has not been observed under all possible environmental conditions. The phenotype may vary somewhat with variations in environment such as temperature and light intensity, without, however, any variance in genotype.

The following traits have been repeatedly observed and are determined to be the unique characteristics of 'Odyhermes'. These characteristics in combination distinguish 'Odyhermes' as a new and distinct cultivar of New Guinea *Impatiens:*

1. Upright, outwardly spreading and mounded plant habit.
2. Vigorous and freely branching habit; dense and bushy growth habit.
3. Dark green-colored leaves.
4. Freely flowering habit.
5. Large dark red-colored flowers that are positioned above and beyond the foliage.

In side-by-side comparisons conducted in De Kwakel, The Netherlands, plants of the new *Impatiens* differed from plants of the female parent selection primarily in plant size as plants of the new *Impatiens* were more compact than plants of the female parent selection.

In side-by-side comparisons conducted in De Kwakel, The Netherlands, plants of the new *Impatiens* differed from plants of the male parent selection primarily in plant size and flower color as plants of the male parent selection were larger and had dark purple-colored flowers.

Plants of the new *Impatiens* can be compared to plants of the New Guinea *Impatiens* cultivar Martinique, disclosed in U.S. Plant Pat. No. 9,149. In side-by-side comparisons conducted in De Kwakel, The Netherlands, plants of the new *Impatiens* differed from plants of the cultivar Martinique in the following characteristics:

1. Plants of the new *Impatiens* were more compact than plants of the cultivar Martinique.

2. Plants of the new *Impatiens* flowered earlier than plants of the cultivar Martinique.
3. Plants of the new *Impatiens* and the cultivar Martinique differed in flower color as plants of the cultivar Martinique had lighter red-colored flowers.

BRIEF DESCRIPTION OF THE PHOTOGRAPH

The accompanying photograph illustrates the overall appearance of the new *Impatiens*. The photograph show the colors as true as it is reasonably possible to obtain in colored reproductions of this type. Colors in the photograph may differ slightly from the color values cited in the detailed botanical description which accurately describe the colors of the new *Impatiens*. The photograph comprises a side perspective view of a typical flowering plant of 'Odyhermes' grown in a container.

DETAILED BOTANICAL DESCRIPTION

In the following description, color references are made to The Royal Horticultural Society Colour Chart, 2001 Edition, except where general terms of ordinary dictionary significance are used. The following observations and measurements describe plants grown in De Kwakel, The Netherlands during the autumn in a glass-covered greenhouse and under conditions and practices which approximate those generally used in commercial New Guinea *Impatiens* production. During the production of the plants, day and night temperatures averaged 18° C. and light levels averaged 220 Watts per square meter. Measurements and numerical values represent averages for typical flowering plants. Single plants were grown in 13-cm pots and were about three months old when the photograph and the detailed description were taken.

Botanical classification: *Impatiens hawkeri* cultivar Odyhermes.

Parentage:

*Female, or seed, parent.*—Proprietary selection of *Impatiens hawkeri* identified as code number 200024, not patented.

*Male, or pollen parent.*—Proprietary selection of *Impatiens hawkeri* identified as code number 200142-01, not patented.

Propagation:

*Type.*—Terminal cuttings.

*Time to initiate roots.*—About eight to nine days at 18° C. to 22° C.

*Time to produce a rooted young plant.*—About 16 days at 18° C. to 22° C.

*Root description.*—Fine; white, close to 155D, in color.

*Rooting habit.*—Freely branching.

Plant description:

*Plant form.*—Upright, outwardly spreading and mounded plant habit.

*Growth and branching habit.*—Vigorous and freely branching habit; about seven lateral branches developing at the base; dense and bushy growth habit. Pinching, that is, removal of the terminal apices, is typically not required, but will enhance branching.

*Plant height.*—About 19 cm.

*Plant diameter or spread.*—About 29 cm.

*Lateral branches.*—Length: About 11 cm. Diameter: About 6 mm. Internode length: About 4 cm. Texture: Smooth, glabrous. Color: Close to 183A.

Foliage description:

*Arrangement.*—Opposite or in whorls, simple.

*Length.*—About 10 cm.

*Width.*—About 3 cm.

*Shape.*—Lanceolate.

*Apex.*—Acuminate.

*Base.*—Attenuate.

*Margin.*—Serrate with ciliation.

*Texture, upper and lower surfaces.*—Smooth, glabrous.

*Venation pattern.*—Pinnate.

*Color.*—Developing and fully expanded foliage, upper surface: 137A; venation, 181D. Developing and fully expanded foliage, lower surface: 137C; venation, 183C.

*Petiole.*—Length: About 3 cm. Diameter: About 2 mm. Texture, upper and lower surfaces: Smooth, glabrous. Color, upper and lower surfaces: 181A.

Flower description:

*Flower type and flowering habit.*—Single axillary flowers. Freely flowering habit; usually about four open flowers and flower buds per lateral branch. Flowers positioned above the foliage and typically face upright or outward. Flowers last about ten days under greenhouse conditions. Petals self-cleaning, gynoecium persistent. Flowers not fragrant.

*Natural flowering season.*—Year-round under greenhouse conditions. In the garden, flowering from spring until fall in The Netherlands. Plants begin flowering about ten weeks after planting.

*Flower size.*—Diameter: About 6 cm. Height: About 5 mm.

*Flower buds.*—Length: About 2 cm. Diameter: About 1.2 cm. Shape: Ovoid. Color: 61C.

*Petals.*—Quantity/arrangement: Five per flower in a single whorl. Length: About 3 cm. Width: About 3 cm. Shape: Obovate to slightly cordate. Apex: Emarginate. Base: Cuneate to obtuse. Margin: Entire. Texture, upper and lower surfaces: Smooth, glabrous. Color: When opening, upper surface: 53A. When opening, lower surface: 61C. Fully opened, upper surface: 46B; color becoming closer to 45B with development. Fully opened, lower surface: 63B.

*Sepals.*—Quantity/arrangement: Two, opposite; one modified into an elongated spur. Length: About 1 cm. Width: About 5 mm. Shape: Ovate. Apex: Acuminate. Base: Obtuse. Margin: Entire. Texture, upper and lower surfaces: Smooth, glabrous. Color, upper and lower surfaces: Close to 183A. Spur length: About 5 cm. Spur diameter: At flower, about 1.3 mm; at apex, about 1 mm. Spur texture: Smooth, glabrous. Spur color: 53A.

*Peduncles.*—Length: About 4 cm. Diameter: About 2 mm. Angle: About 45° from vertical. Strength: Strong. Texture: Smooth, glabrous. Color: Close to 183A.

*Reproductive organs.*—Stamens: Quantity: Five fused at anthers; filaments free. Anther length: About 5 mm. Anther color: 4C blushed with 45C. Pollen amount: Abundant. Pollen color: Close to 155D. Pistils: Quantity per flower: One. Pistil length: About 5 mm. Stigma shape: Rounded. Stigma color: 155B. Style color: 155B. Ovary color: Close to 144A.

*Seed/fruit.*—Seed and fruit production have not been observed.

Disease/pest resistance: Plants of the new *Impatiens* have not been observed to be resistant to pathogens and pests common to New Guinea *Impatiens*.

Temperature tolerance: Plants of the new *Impatiens* have been observed to tolerate temperatures from about 8° C. to about 35° C.

It is claimed:

1. A new and distinct New Guinea *Impatiens* plant named 'Odyhermes' as illustrated and described.

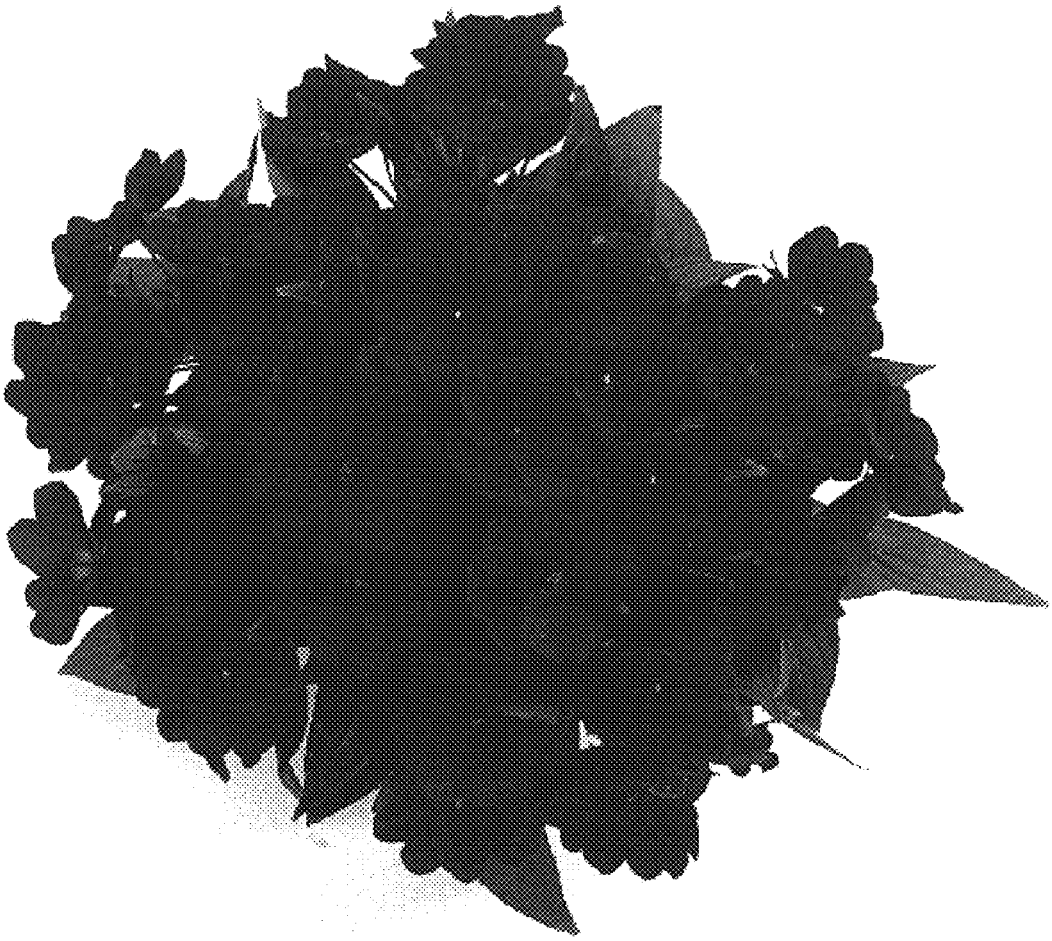

* * * * *